United States Patent [19]

Jessop et al.

[11] 4,277,440

[45] Jul. 7, 1981

[54] METERING APPARATUS

[75] Inventors: Thomas C. Jessop, Webster; William L. Smith, Rochester, both of N.Y.

[73] Assignee: Eastman Kodak Company, Rochester, N.Y.

[21] Appl. No.: 54,064

[22] Filed: Jul. 2, 1979

[51] Int. Cl.³ .......................... G01N 35/00; G01N 1/14
[52] U.S. Cl. .................................. 422/100; 73/864.18; 141/130; 422/63; 422/103
[58] Field of Search ...................... 422/63, 64, 65, 100, 422/101, 103, 66; 141/130; 222/477, 70, 71; 73/425.4 R

[56] References Cited

U.S. PATENT DOCUMENTS

| 949,545 | 2/1910 | Muller . | |
|---|---|---|---|
| 1,668,511 | 5/1928 | McLaughlin . | |
| 2,475,730 | 7/1949 | Wandrey . | |
| 2,718,299 | 9/1955 | Atwater et al. . | |
| 2,739,485 | 3/1956 | Sensebusch . | |
| 2,866,345 | 12/1958 | Woods . | |
| 3,192,968 | 7/1965 | Baruch et al. | 422/64 |
| 3,203,257 | 8/1965 | Geyer . | |
| 3,211,269 | 10/1965 | Emig . | |
| 3,323,373 | 6/1967 | Murray et al. . | |
| 3,475,130 | 10/1969 | Baruch | 422/64 |
| 3,683,977 | 8/1972 | Crowe et al. . | |
| 3,963,148 | 6/1976 | Proni et al. | 422/63 |
| 3,992,158 | 11/1976 | Przybylowicz et al. . | |
| 3,994,687 | 11/1976 | Engelbrecht | 422/63 |
| 3,998,238 | 12/1976 | Nigro . | |
| 4,042,152 | 8/1977 | Drbal | 422/63 |
| 4,053,381 | 10/1977 | Hamblen | 204/195 M |
| 4,099,548 | 7/1978 | Sturm et al. | 73/425.6 |
| 4,110,167 | 8/1978 | Melnyk . | |
| 4,142,656 | 3/1979 | Smith et al. | 222/325 |
| 4,152,390 | 5/1979 | Nosco et al. | 422/63 |

Primary Examiner—Ronald Serwin
Attorney, Agent, or Firm—D. D. Schaper

[57] ABSTRACT

Apparatus is disclosed which is adapted to repeatedly and accurately dispense predetermined amounts of fluid, especially biological fluids, onto generally planar test elements. The apparatus comprises a metering pump actuated by an escapement mechanism which moves the pump in precise increments. The fluids are dispensed through a pair of metering tips which are spaced a given distance from the test element.

15 Claims, 9 Drawing Figures

METERING APPARATUS

CROSS-REFERENCES TO RELATED APPLICATIONS

Reference is made to commonly-assigned U.S. patent application; Ser. No. 927,702, entitled CHEMICAL ANALYZER, filed in the name of Schnipelsky et al., on July 24, 1978.

BACKGROUND OF THE INVENTION

1. Field of the Invention

This invention relates to the chemical analysis of substances, and more particularly, to apparatus for the precise metering of biological fluids onto test elements.

2. State of the Prior Art

A number of automated systems have been developed for performing quantitative chemical analyses of fluid samples. Most of the commercially available systems utilize liquid reagents and require analyzer equipment having intricate solution handling and transport capabilities. Recent developments, however, have provided test elements in essentially planar, dry form which can be loaded into a cartridge for use in an analyzer. In the use of such an analyzer, a test element from a cartridge is fed into a metering station where a predetermined amount of sample fluid is deposited on the test element. After an incubation period, the element is moved to a read station where a change in the test element is measured, the amount of change being proportional to a particular analyte in the fluid. The test element is used only once and is discarded after the reading has been taken. An analyzer for use with such test elements is disclosed in commonly-assigned U.S. Pat. No. 4,152,390, granted May 1, 1979.

Test elements of the type described above are adapted to function with very small quantities of fluid. For example, test elements for performing colorimetric analyses can produce a measurable response with only 10 microliters of sample fluid, and elements for performing potentiometric analyses are operable with 10 microliters of sample fluid and 10 microliters of reference fluid. Very precise metering devices are required for use with the test elements, since the volume of fluid supplied to the elements should preferably not vary more than five percent from a selected value to achieve desirable test results. Further, in automated and in multi-channel analyzers the metering devices must be capable of repeatedly and accurately dispensing micro-quantities of fluid onto a series of test elements.

A metering device for use with planar test elements is shown in commonly-owned U.S. Pat. No. 4,142,656, granted to Smith et al., on Mar. 6, 1979. In this patent, fluid is dispensed from a sample cup having a dispensing tip formed on a bottom wall thereof. An electrically-actuated pump is used to generate a pressure in the cup sufficiently above ambient to form a pendant drop on the cup. The test element is then moved into contact with the pendant drop to effect a transfer of the fluid to the element. Both the sample cup and the test element are transported to the metering apparatus. The metering device disclosed in the Smith et al. patent requires complex transport and drive elements for both the sample cup and the test element, and it is not intended for use in applications where fluid must be aspirated into the metering system.

There is a need for precise metering apparatus which is suitable for use on relatively small, portable analyzers. Such analyzers are used in operating rooms for emergency tests, or carried in ambulances for field use. Preferably, the metering apparatus for these analyzers should be simple and manually actuated, since power may not be available. Known metering apparatus of this type often lacks the precision required for acceptable results. One of the main problems with manually-actuated metering devices is that the volume of fluid delivered varies with the speed of actuation; thus, results vary with different operators and from one metering operation to the next. Patents relating to relatively simple metering devices include: U.S. Pat. No. 3,683,977, granted on Aug. 15, 1972; and U.S. Pat. No. 4,110,167, granted on Aug. 29, 1978.

OBJECTS OF THE INVENTION

It is an object of the present invention to overcome the above-described problem in prior-art devices, and to provide a novel and improved apparatus for the repeated, precise dispensing of micro-quantities of fluid.

It is another object of the invention to provide apparatus for the precise dispensing of a predetermined quantity of fluid in which the apparatus is adapted to expel a portion of said quantity in a first period of a dispensing cycle and to expel the remainder of said quantity in a second period of the cycle.

Yet another object of the invention to provide apparatus for the precise dispensing of a predetermined quantity of fluid from a metering tip in which the apparatus is adapted to create a first pressure condition in the metering tip in a first period of a dispensing cycle and to create a second pressure condition in the tip in a second period of the cycle to expel the fluid from the tip.

Still another object of the invention is to provide means in a metering apparatus for discharging a quantity of fluid immediately after aspiration to insure that the apparatus is primed for a precise metering operation.

A further object of the invention is to provide a manually-actuated metering apparatus which has a dispensing cycle of uniform duration.

A still further object of the invention is to provide a metering apparatus which is particularly suitable for substantially simultaneously metering predetermined quantities of a sample fluid and a reference fluid onto a substrate.

Other objects and advantages will become apparent from the following Summary and Description of the Preferred Embodiments, when considered in the light of the attached drawings.

SUMMARY OF THE INVENTION

This invention relates to a metering or dispensing apparatus for repetitive, precise dispensing of micro-quantities of sample fluids. More specifically, the invention relates to apparatus for the metering of biological fluids onto generally planar test elements.

In accordance with one aspect of the invention, there is provided metering apparatus for dispensing a predetermined quantity of fluid onto a substrate spaced a given distance from the apparatus, the apparatus comprising: a metering tip having a fluid chamber for receiving fluid aspirated into the tip through an aperture therein; pump means in fluid communication with the metering tip, the pump means being adapted to aspirate fluid into the tip and to expel fluid therefrom; and drive means for moving the pump means through a plurality of positions and for stopping the pump means in each of the positions, the pump means being adapted to expel a first portion of the quantity during movement of the pump means from a first position to a second position and the remainder of the quantity during movement of the pump means from the second position to a third position.

In one embodiment of the invention, the pump means for aspirating and dispensing sample fluid comprises a pair of cylinders with plungers movable therein. A drive means, for advancing the pump means in precise increments, includes an escapement mechanism which is movable in a first direction to aspirate sample fluid into the metering tip and is adapted to be moved in the opposite direction through a series of positions to successively deposit fluid onto a selected number of test elements. The escapement mechanism comprises a ratchet rod connected to the pump means through a pair of flexible connectors which provide for any misalignment in the system. A pair of pivotally mounted bars on opposite sides of the rod cooperate with ratchet teeth on the rod to control movement of the rod. The bars are disengaged from the ratchet rod when fluid is being aspirated into the metering tip. A quantity of sample fluid is expelled back into the sample container, prior to the start of the metering operation; this insures that the metering tip is primed and that the first test element receives a precise amount of fluid.

DESCRIPTION OF THE PREFERRED EMBODIMENT

The invention is described hereinafter in connection with an analyzer for performing quantitative chemical analyses of biological fluids such as blood serum. However, the invention is not so limited, and it can also be employed in other types of apparatus where precise metering devices are required.

The invention is particularly useful with potentiometric analyzers in which case the substrate which makes the test possible comprises a pair of electrodes selective to the ion activity of choice. Recent developments have provided the electrodes in essentially planar, dry form suitable for use in pairs in an analyzer. Such an analyzer is described and claimed in the aforesaid U.S. patent application, Ser. No. 927,702, entitled CHEMICAL ANALYZER. The invention can also be employed in an analyzer using a radiometric detector which will read a suitable substrate incorporating, for example, reagents that create a dye in proportion to the analyte being measured. An analyzer of this type is disclosed in the aforesaid commonly-assigned U.S. Pat. No. 4,152,390.

One form of test element for use with the apparatus of the subject invention is disclosed in the patent to Hamblen et al., U.S. Pat. No. 4,053,381, granted Oct. 11, 1977. This patent describes a test element, or analysis slide, of the type which is used to potentiometrically designate the activity of ions in a liquid test solution by the use of electrodes. The invention can also be used with other forms of test elements, as for example, the element disclosed in the commonly-owned U.S. Patent to Przybylowicz et al., U.S. Pat. No. 3,992,158, granted on Nov. 16, 1976. The test element disclosed in this patent is formed as a multi-layer element containing the necessary reagents for reaction with components of a biological fluid, such as blood serum, deposited thereon. Certain reactions colorimetrically produce a change in optical density in the element which is sensed by a reflectometer, the amount of light reflected from the element varying in accordance with the reaction and being indicative of the amount of a particular analyte present in the fluid.

Figure 1:
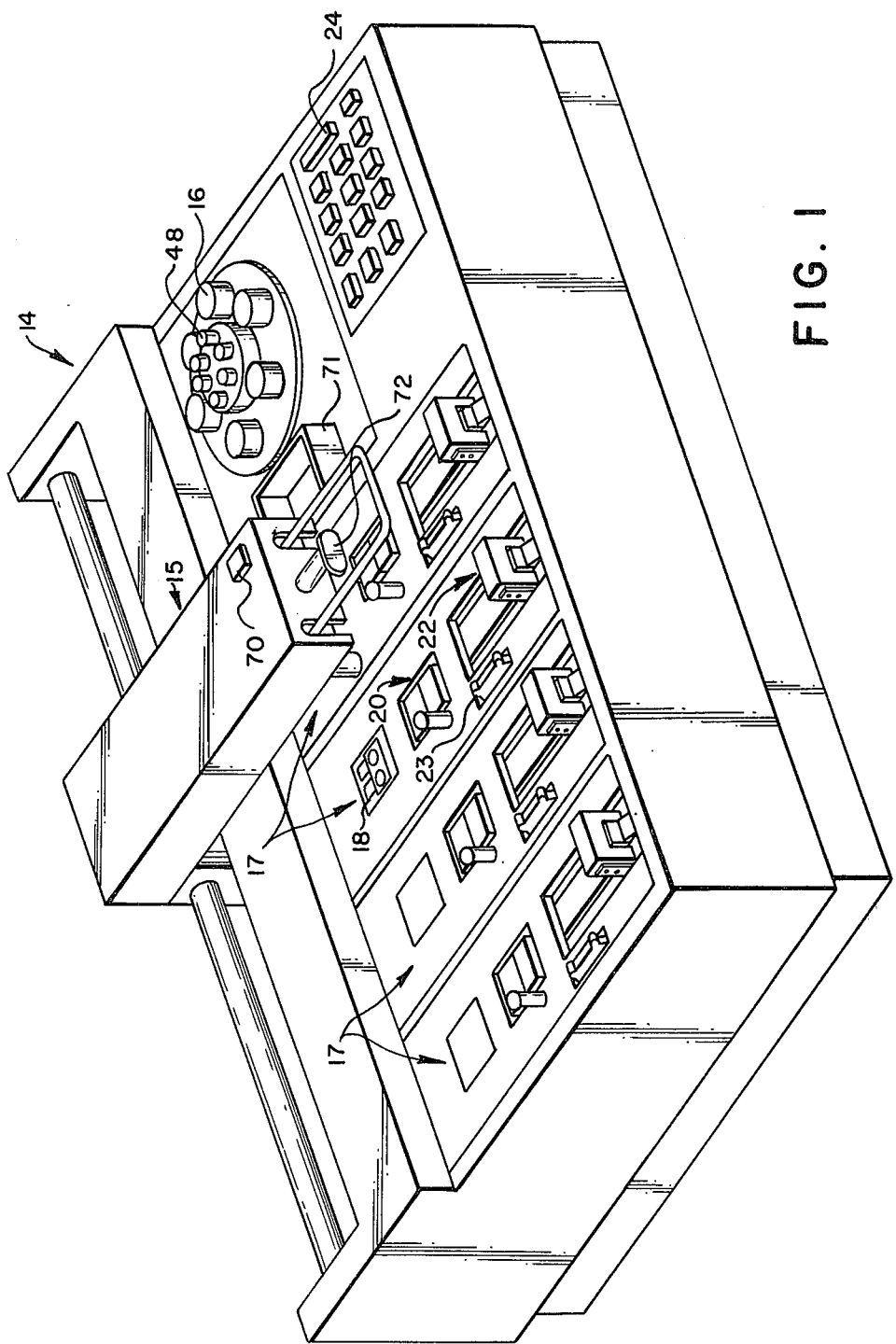
FIG. 1 is a perspective view of a chemical analyzer of a type which is adapted to employ the metering apparatus described herein.
Figure 2:
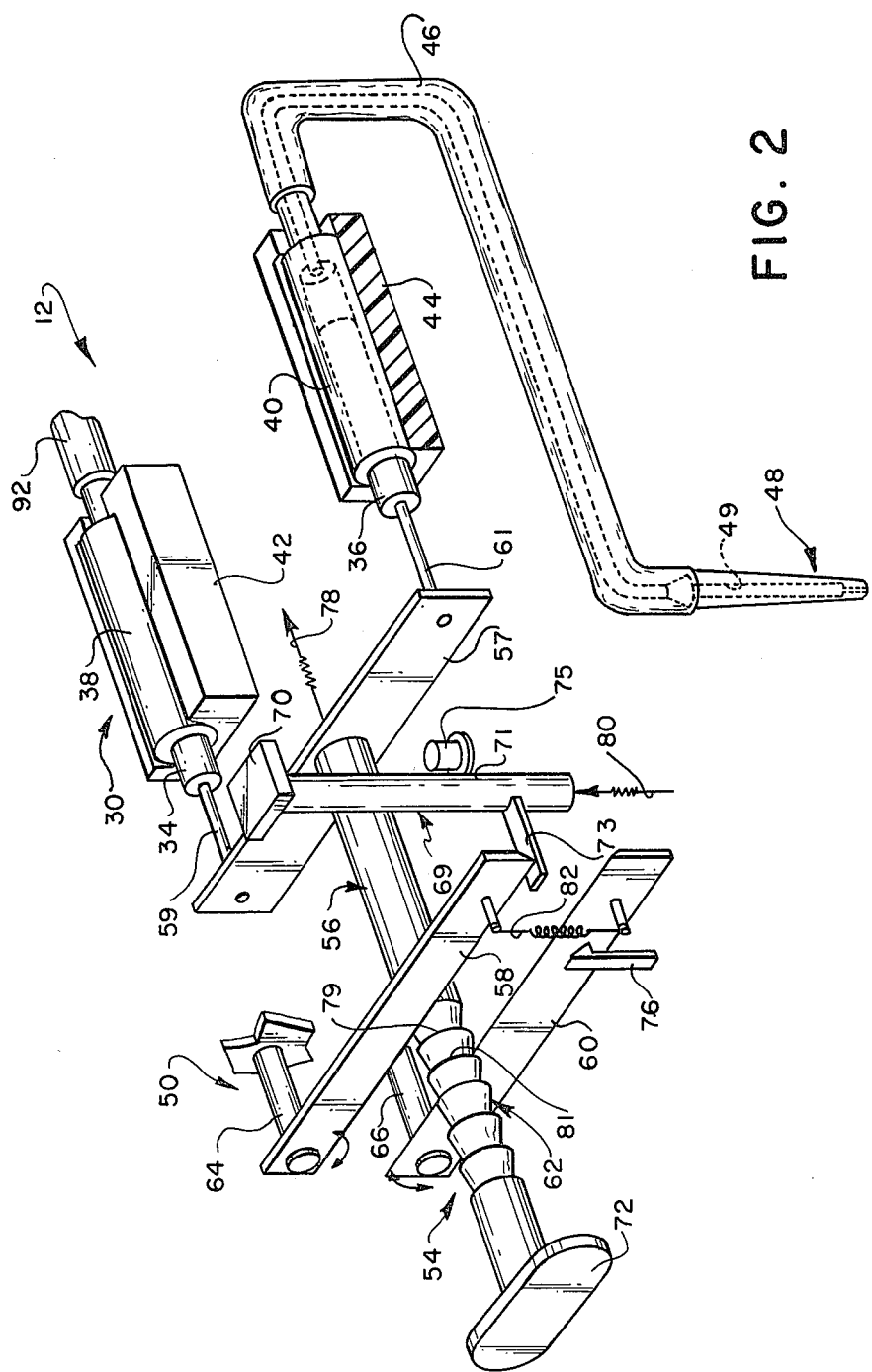
FIG. 2 is a perspective view, shown partially in section, of the metering apparatus of the subject invention.

In accordance with a preferred embodiment of the invention, there is shown in FIG. 2 a metering apparatus 12 constructed in accordance with the invention. Metering apparatus 12 is adapted to be used in a potentiometric analyzer 14 of the type shown in FIG. 1.

With reference to FIG. 1, the analyzer 14 comprises a housing 15 which is adapted to support metering apparatus 12 for movement in the analyzer. Metering apparatus 12 is adapted to draw in, or aspirate, a supply of sample fluid from a cup 16. The metering apparatus is then moved to a metering position where it substantially simultaneously deposits a predetermined quantity of sample fluid and a predetermined quantity of reference fluid onto a test element 18 in the metering position. After an incubation period, a potentiometric reading of the test element is taken by an electrometer, not shown. As shown in FIG. 1, analyzer 14 comprises four channels 17, and thus, metering apparatus 12 can be used to sequentially dispense fluid onto the elements 18 in each of the channels. Test elements 18 are mounted on analyzer 14 in cartridges 20 and are sequentially fed from the cartridges and advanced through the analyzer by means of a slide transfer mechanism 22. A control knob 23 is used to program the analyzer 14 for the desired test, as disclosed in U.S. patent application Ser. No. 37,250, entitled CHEMICAL APPARATUS, filed in the name of Jessop, on May 9, 1979. A keyboard 24 is used by the operator to provide input data to analyzer 14.

Metering apparatus 12 must be capable of repeatedly and accurately dispensing very small quantities of fluids; for example, test element 18 is adapted to be operable with 10 microliters of reference fluid and 10 microliters of sample fluid. As shown in FIG. 2, apparatus 12 comprises a pump means 30 which includes a first plunger 34 movable in a cylinder 38 and a second plunger 36 movable in a cylinder 40. Cylinders 38 and 40 are supported respectively on blocks 42 and 44, in the apparatus. A conduit 46 connects the pump cylinder 40, to a metering tip 48. A second conduit 92 connects cylinder 38 to a reference fluid dispensing device 90 (FIG. 4), as will be explained in more detail hereinafter.

A new metering tip 48 is used with each new sample fluid. The tip 48 includes a fluid chamber 49 for receiving the quantity of sample fluid required so that no sample fluid is drawn into tube 46 or cylinder 40. Thus, there is no sample carry-over from one sample to the next.

A drive means 50 provides means for moving pump plunger 36 in a first direction to aspirate sample fluid into metering tip 48, and in a second direction to dispense fluid from tip 48. Plunger 34 is moved with plunger 36 and functions to dispense reference fluid, as explained below. Drive means 50 comprises an escapement mechanism 54 which includes a ratchet rod 56, restraining bars 58, 60, and a return spring 78 which is tensioned during the aspiration of sample fluid into tip 48. Restraining bars 58, 60 are pivotally mounted respectively at 64 and at 66, and the bars are biased toward each other by a spring 82; bars 58, 60 are adapted to cooperate with ratchet teeth 62 on rod 56 to control movement of the rod in a metering operation. Rod 56 is connected to plungers 38, 40, through a crosspiece 57 and a pair of connectors 59, 61, which are of a flexible construction to compensate for any misalignment between drive means 50 and pump means 30.

Escapement mechanism 54 is actuated by a release pin 69 which comprises a shaft 71 having dispense button 70 affixed to its upper end. (See FIG. 2.) Dispense button 70 is adapted to be depressed by the operator to initiate the dispensing cycle; button 70 is released immediately upon reaching a fully depressed position to start the second portion of the dispensing cycle. "Dispensing cycle" is used herein to refer to the sequence of movements which occur in the elements of metering apparatus 12 for the dispensing of fluid onto a single test element. A projection 73 on shaft 71 contacts bars 58 and 60 during the dispensing cycle to move the bars out of engagement with rod 56. A handle 72, mounted on ratchet rod 56, can be grasped by the operator to retract rod 56 for aspirating fluid into tip 48. A latch 76 is provided to hold bar 60 out of contact with teeth 62 during the aspiration of sample fluid.

Figure 3A:
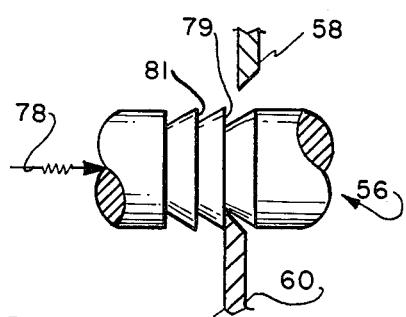
FIGS. 3a through 3f show the relative positions of elements of the escapement mechanism during a single dispensing cycle.

In the aspiration of fluid into tip 48, ratchet rod 56 is moved to the left, as shown in FIG. 2, until pistons 34, 36, are fully retracted and crosspiece 57 is in contact with a stop 75. Just before crosspiece 57 contacts stop 75, latch 76 is disengaged from bar 60 which then moves into contact with rod 56. When aspiration is complete and handle 72 is released, rod 56 moves to the right under the action of a return spring 78 until a first ratchet tooth 79 is contacted by bar 60, as shown in FIG. 3a. As a result of this initial movement of rod 56, a certain amount of fluid in tip 48 will be discharged back into the sample cup 16; this serves to prime the system so that the first quantity dispensed will be the same volume as that of successive quantities.

Figure 3B:
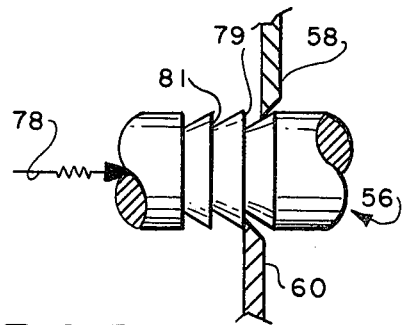
Figure 3C:
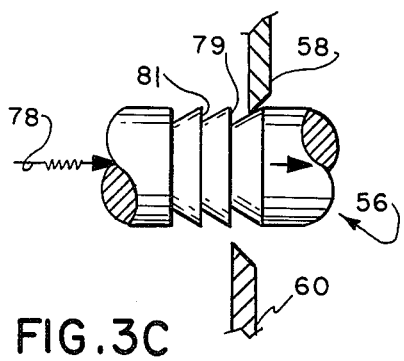
Figure 3D:
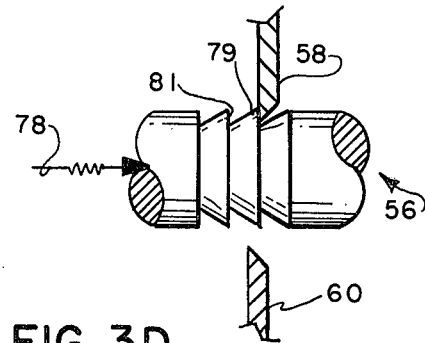

The sequence which rod 56 and bars 58, 60, pass through in a dispensing cycle is shown in FIGS. 3a through 3f. FIG. 3a shows the bars 58, 60, in the rest position, with bar 58 out of engagement with rod 56 and bar 60 engaged with tooth 79 to prevent movement of rod 56 by return spring 78. FIG. 3b shows bar 58 in engagement with rod 56; this occurs when projection 73 is disengaged from bar 58 just after the operator has started to depress button 70. With the elements in the positions shown in FIG. 3b, rod 56 is prevented from moving to the right by bar 60. FIG. 3c shows the positions of bars 58, 60, when dispense button 70 is fully depressed; bar 60 has been moved out of engagement with rod 56 by projection 73. Return spring 78 is now free to move rod 56 to the position shown in FIG. 3d which results in a first quantity of fluid being expelled from tip 48.

Figure 3E:
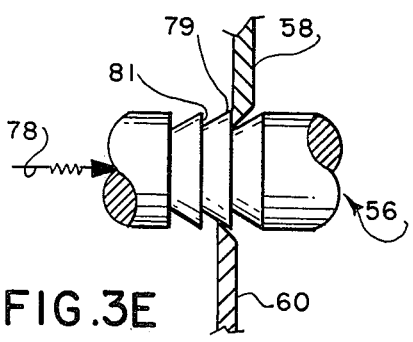
Figure 3F:
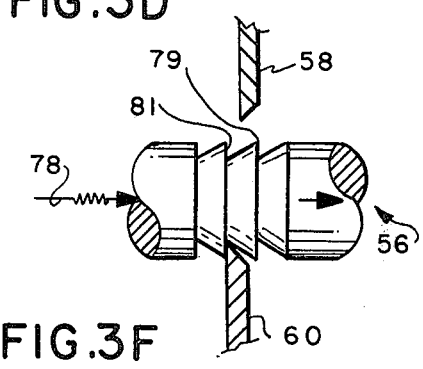

When dispense button 70 is released by the operator, the button moves upward under the action of spring 80; as soon as projection 73 moves out of contact with bar 60, bar 60 is moved, by spring 82, into engagement with rod 56, as shown in FIG. 3e. As the dispense button 70 continues its upward movement, projection 73 contacts bar 58, moving it out of engagement with tooth 79 and allowing ratchet rod 56 to move until stopped by the abutment of lower bar 60 against tooth 81, as shown in FIG. 3f. The second movement of rod 56 causes a second quantity of fluid to be expelled and completes the dispensing cycle.

As will be apparent from the foregoing description, each dispensing cycle comprises two movements of ratchet rod 56. The first movement occurs when the dispense button 70 is depressed, and the second occurs when the button is released. The ratio of the distance of the first movement to the distance of the second movement is controlled by the axial spacing between the restraining bars 58, 60. The total distance moved is the same in each cycle and is equal to the pitch of the ratchet teeth 62. The ratio can be controlled to correspond to the system needs. In one illustrative embodiment, ratchet rod 56 moves 40% of the total distance on the first movement and 60% on the second; to achieve this ratio of movement, the axial spacing between bars 58 and 60 must be less than one half the pitch of teeth 62.

When the metering operations for a particular sample fluid have been completed, metering tip 48 is discarded by an ejection means, not shown, into a receptacle 71. (See FIG. 1.) During the discard operation, a linkage, not shown, pulls bar 60 away from rod 56 and into engagement with latch 76. Since bar 58 is also prevented from engaging rod 56 by release pin 69, ratchet bar 56 and pistons 38, 40, are moved to a fully extended position by spring 78. In the aspiration of fluid into tip 48, latch 76 will not be disengaged until handle 72 is fully retracted. This latching feature assures that a full charge of fluid is drawn into tip 48.

Figure 4:
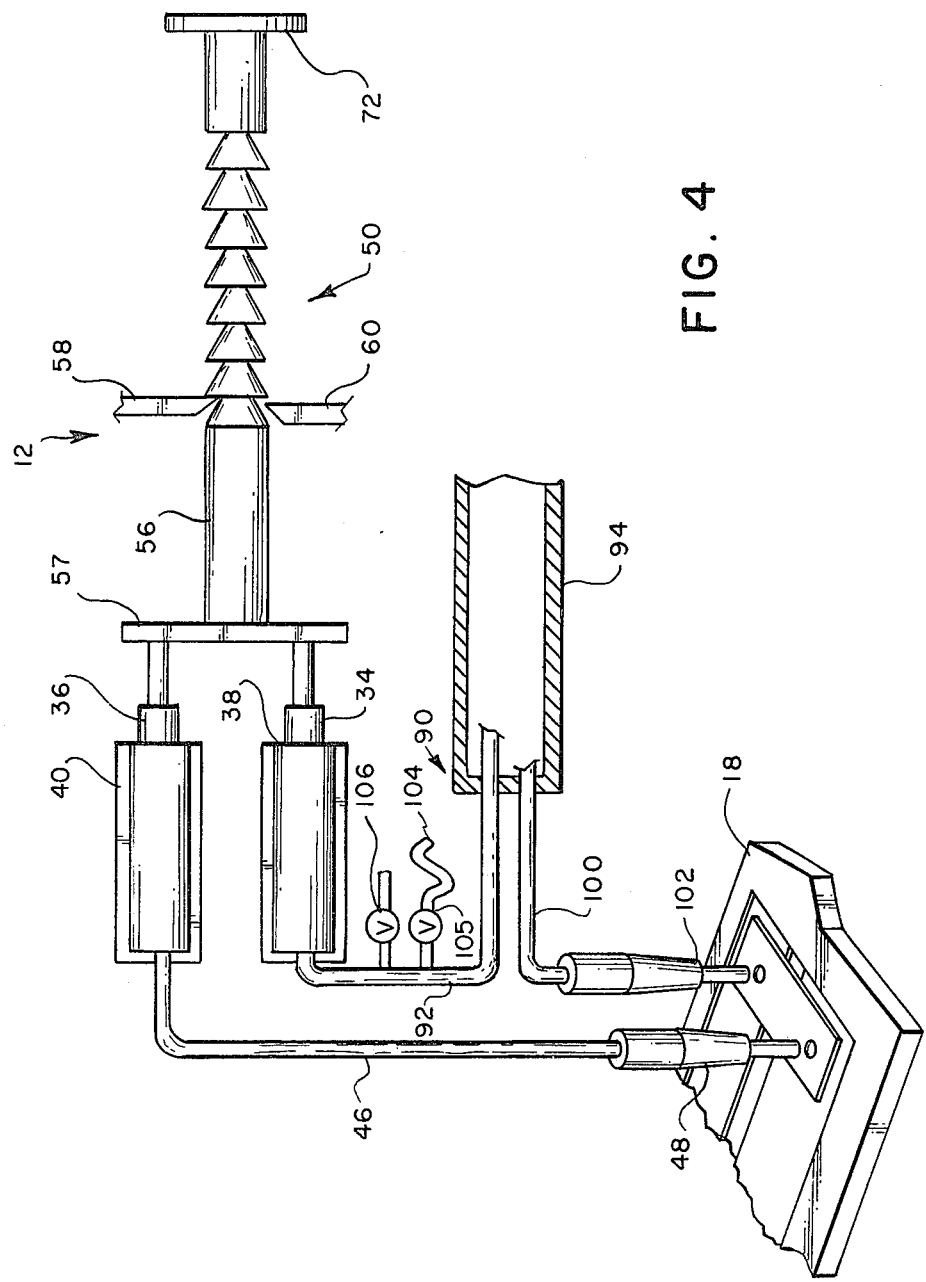
FIG. 4 is a schematic view of the metering apparatus, showing the pump means, the sample fluid metering tip, and the reference fluid dispensing device.

With reference to FIG. 4, there is shown a schematic view of metering apparatus 12 which includes a reference fluid dispensing device 90. Device 90 comprises a reference fluid supply container 94 which is adapted to contain sufficient reference fluid for normal operation of the analyzer during a 12-hour period. Container 94 is connected to cylinder 38 by a conduit 92 and to a reference fluid metering tip 102 through conduit 100. A labyrinth 105, connected to conduit 92, is formed from a small diameter metal tubing to provide a vent to the reference fluid such that pressure will be at atmospheric on the interior of container 94. A dump valve 106 is opened when fluid is aspirated into sample tip 48 to prevent air from being drawn into reference fluid dispensing tip 102. During a dispensing cycle, valve 106 and a valve 104 on labyrinth 105 are closed, and pump means 30 is indexed to dispense fluid from both the sample tip 48 and the reference fluid dispensing tip 102 in the manner described above for tip 48.

As previously described, under most operating conditions, a first quantity of fluid is expelled in the first movement of the escapement mechanism 50 and the remainder of the fluid is expelled on the second movement. The first quantity will, in many instances, remain on the tip as a pendant drop. Under some operating conditions, however, the first movement may simply pressurize the system, with little or no fluid being moved out of the tip; in this case the fluid is expelled during the second movement of the escapement mechanism.

With reference to FIG. 4, tips 48 and 102 are shown in the metering position over a test element 18 of the potentiometric type. During the metering of fluid, tips 48 and 102 are spaced from the test element 18 such that, under some metering conditions, fluids bridge the gap between tips 48, 102, and element 18 during the metering operation.

In operation of metering apparatus 12, the metering apparatus is first positioned over a sample cup on analyzer 14. The operator then moves handle 72 to aspirate a supply of sample fluid into metering tip 48. When the metering tip is charged with sample fluid, apparatus 12 is moved to a metering position over a test element 18 in one of the channels 17. Dispenser button 18 is depressed and released to dispense a predetermined quantity of fluid onto the test element. If additional tests are desired, the operation can be repeated in the other channels 17.

One of the most important elements in insuring that a precise amount of fluid is delivered to test element 18 is the speed at which the pump plungers are moved. A relatively fast, controlled movement of the plungers has been found desirable. It is preferable for the fluid to be delivered in a continuous stream, rather than several small drops, and this can be accomplished by a fast movement of the plunger. The metering apparatus disclosed herein is particularly suitable for the precise dispensing of very small quantities of fluids, since the time of each dispensing cycle is controlled by the escapement mechanism 50, and not by the speed at which the operator depresses the dispense button 70.

The invention has been described in detail with particular reference to preferred embodiments thereof, but it will be understood that variations and modifications can be effected within the spirit and scope of the invention.

What is claimed is:

1. A metering device for use in apparatus for the analysis of biological fluids, said device being adapted to meter a predetermined quantity of fluid onto a test element containing reagents for the testing of a particular analyte, said analyzer being adapted to measure a change in said element which is indicative of the amount of analyte in said fluid, said device comprising:
   a metering tip having a fluid chamber for receiving fluid aspirated into said tip through an aperture therein;
   pump means in fluid communication with said metering tip, said pump means being adapted to draw fluid into said tip and to expel fluid therefrom in precise amounts; and
   drive means operatively connected to said pump means, said drive means including an escapement mechanism which is adapted to advance said pump means through a plurality of steps to deliver said quantity of fluid to each of a plurality of test elements, each quantity of fluid being delivered by advancement of said pump means through a first step which expels a first portion of said quantity of fluid from said tip and advancement of the pump means through a second step which expels the remainder of said quantity from the tip.

2. A metering device, as defined in claim 1, wherein said escapement mechanism comprises a rod having ratchet teeth thereon and a pair of restraining bars which cooperate with the teeth.

3. A metering device, as defined in claim 2, wherein said bars are connected by a spring and a release pin is operatively associated with said bars to effect movement of the rod through said steps.

4. Metering apparatus, as recited in claim 2, wherein said rod includes a longitudinal axis, and said bars are spaced relative to each other and to the teeth on said rod in a direction along said axis such that advancement of said pump means during said first step is less than the advancement during said second step.

5. Metering apparatus, as recited in claim 2, wherein said pump means comprises a cylinder and a plunger therein which is movable through each of said steps, and said escapement mechanism is connected to said plunger by a flexible connection which compensates for misalignment between the escapement mechanism and the plunger.

6. Metering apparatus, as defined in claim 2, wherein said rod is movable in a first direction to aspirate fluid into said tip and in an opposite direction to dispense fluid from the tip, spring means is provided for biasing said rod in said opposite direction, and said restraining bars are operable on said rod to control movement of the rod in said opposite direction.

7. Metering apparatus, as recited in claim 6, wherein stop means is provided for limiting movement of said rod in said first direction after aspiration of said fluid, and the rod is movable in said opposite direction for a given distance away from the stop means before contacting said bars whereby a quantity of fluid will be discharged from the tip to prime the apparatus for a metering operation.

8. Metering apparatus, as recited in claim 6, wherein means is provided for disengaging said bars from said rod when the rod is moved in said first direction.

9. A metering device for use in a chemical analyzer in which fluids are dispensed onto a test element for determining the activity of ions in a test fluid, said element comprising a pair of electrodes and being adapted to receive a predetermined quantity of sample fluid and a predetermined quantity of reference fluid, said device having reference fluid storage means and sample fluid storage means, said device comprising:
   a pair of metering tips through which the fluids are dispensed onto said element, one of said tips being in fluid communication with the reference fluid storage means and the other of said tips being in fluid communication with the sample fluid storage means;
   pump means in fluid communication with said metering tips and said storage means; and
   drive means operatively connected to said pump means, said drive means being adapted to operate said pump means in a first mode to aspirate fluid into said sample fluid storage means and in a second mode to substantially simultaneously deposit said quantities of reference fluid and sample fluid onto said element, and said drive means including means for moving said pump means through a series of steps in said second mode and for stopping said pump means at the completion of each step.

10. A metering device, as defined in claim 9, wherein said pump means includes a pair of plungers connected to said drive means.

11. A metering device, as defined in claim 9, wherein said drive means includes an escapement mechanism for moving said pump means through said steps.

12. A metering device, as defined in claim 9, wherein a dump valve is connected between said pump means and said reference fluid storage means and said valve is opened during the aspiration of fluid by said pump means.

13. Metering apparatus for dispensing a predetermined quantity of fluid onto a substrate spaced a given distance from the apparatus, said apparatus comprising:

a metering tip for receiving fluid aspirated into the tip through an aperture therein;

pump means in fluid communication with said metering tip, said pump means being adapted to aspirate fluid into said tip and to expel fluid therefrom; and drive means for actuating said pump means for a plurality of discrete periods of precisely controlled duration and for stopping said pump means at the end of each of said periods, said pump means being adapted to expel a portion of said quantity from said tip during a first period and the remaining portion during a second period following said first period, and said first period being of a different duration from said second period.

14. Metering apparatus, as recited in claim 13, wherein said drive means comprises a spring for actuating said pump means, and manually movable means for effecting said aspiration and tensioning said spring.

15. Metering apparatus for dispensing a predetermined quantity of fluid onto a substrate spaced a given distance from the apparatus, said apparatus comprising:

a metering tip for receiving fluid aspirated into the tip through an aperture therein;

pump means in fluid communication with said metering tip, said pump means being adapted to aspirate fluid into said tip and to expel fluid therefrom; and drive means for actuating said pump means, said drive means being adapted to impart a two-step movement to said pump means in dispensing said quantity of fluid, the first step creating a first pressure condition in said metering tip, the second step creating a second pressure condition sufficiently above ambient to dispense said quantity of fluid, and said drive means stopping movement of said pump means between each step.

* * * * *